United States Patent [19]

Chin et al.

[11] Patent Number: 4,821,721
[45] Date of Patent: Apr. 18, 1989

[54] APPARATUS AND METHOD FOR APPLYING HEMOSTATIC SCALP CLIPS

[75] Inventors: Albert K. Chin, Palo Alto; Robert K. Goldman, Menlo Park, both of Calif.

[73] Assignee: Thomas J. Fogarty, Palo Alto, Calif.

[21] Appl. No.: 58,263

[22] Filed: Jun. 4, 1987

Related U.S. Application Data

[63] Continuation-in-part of Ser. No. 691,416, Jan. 14, 1985, Pat. No. 4,671,278.

[51] Int. Cl.⁴ ............................................... A61B 17/10
[52] U.S. Cl. .................................. 128/334 R; 128/325; 29/243.56; 227/DIG. 1
[58] Field of Search ............ 128/325, 326, 337, 334 R, 128/346; 227/DIG. 1; 72/410; 29/243.56

[56] References Cited

U.S. PATENT DOCUMENTS

| | | | |
|---|---|---|---|
| 3,802,437 | 4/1974 | Kees | 128/325 |
| 4,166,466 | 9/1979 | Jarvik | 128/325 |
| 4,217,902 | 8/1980 | March | 128/337 X |
| 4,427,008 | 1/1984 | Transue | 128/325 |
| 4,508,253 | 4/1985 | Green | 227/19 |
| 4,530,453 | 7/1985 | Green | 227/19 |
| 4,637,395 | 1/1987 | Caspar et al. | 128/325 X |

FOREIGN PATENT DOCUMENTS

| | | | |
|---|---|---|---|
| 2730691 | 1/1978 | Fed. Rep. of Germany | 128/325 |
| 01280 | 4/1984 | World Int. Prop. O. | 128/325 |

Primary Examiner—Michael H. Thaler
Attorney, Agent, or Firm—Limbach, Limbach & Sutton

[57] ABSTRACT

Apparatus and method for hemostatically clipping an incision edge with clips having jaws normally biased together. A plurality of the clips are contained in a magazine and selectively discharged from the magazine through a tunnel which spreads the jaws of the clips prior to discharge. In operation the spread jaws of the clips are engaged around the incision edge and, upon being discharged from the apparatus, retract to grip the edge.

7 Claims, 1 Drawing Sheet

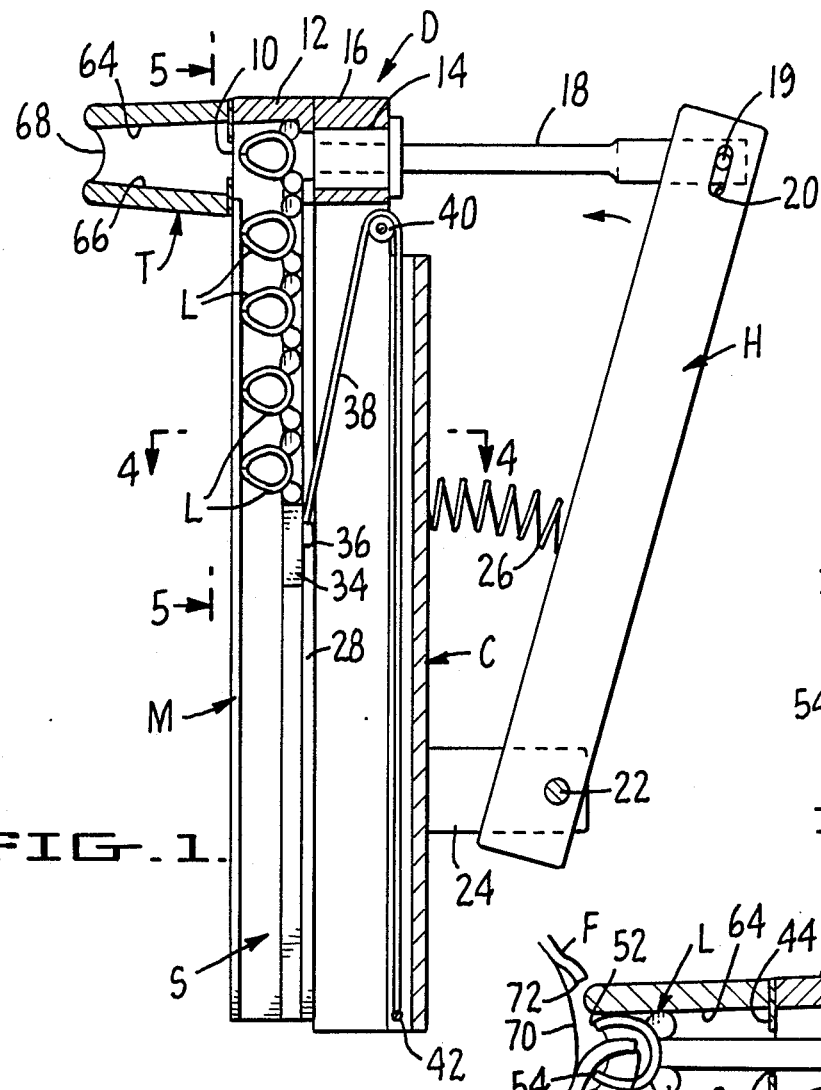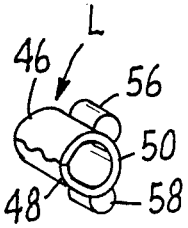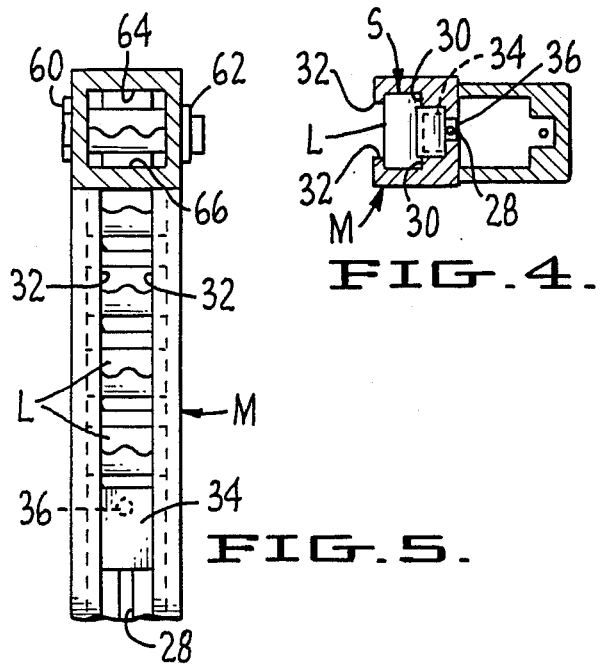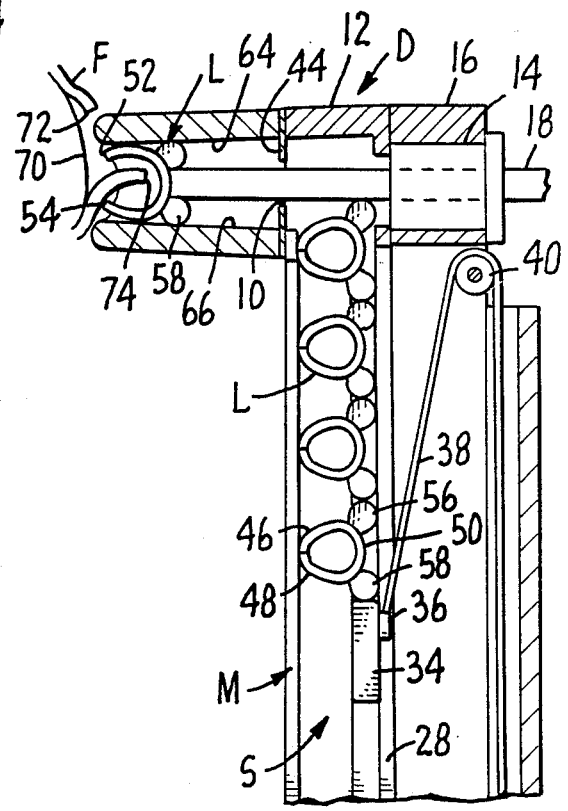

ary of the Invention-->

APPARATUS AND METHOD FOR APPLYING HEMOSTATIC SCALP CLIPS

RELATED APPLICATION

This application is a continuation-in-part of U.S. Application Ser. No. 691,416, filed Jan. 14, 1985, for SCALP HEMOSTATIC CLIP AND DISPENSER THEREFORE, by Albert K. Chin., one of the inventors herein. That application was granted as U.S. Pat. No. 4,671,278 on June 9, 1987.

TECHNICAL FIELD OF THE INVENTION

This invention relates to apparatus and methods used in neurosurgery and, in particular, to an improved hemostatic scalp clip dispenser which is adapted to successively apply multiple clips to the edge of an incision.

BACKGROUND OF THE INVENTION

The present invention is an improvement over that of co-pending application Ser. No. 691,416 in that it is designed for use with standard "Leroy-Raney" clips and employs a dispenser wherein the clips are contained in a magazine and expelled singly. The dispenser uses a piston to push the clips through a tapered tunnel. Passage through the tunnel forces the clip jaws open. An indentation in the distal end of the tunnel accommodates the cut scalp edge. When a clip is completely expelled from the tunnel, it clamps onto the section of the scalp which lies between the sides of the tunnel. Release of the piston allows the next clip in the magazine to be advanced into position. A flexible diaphragm or stop keeps the leading clip in position until the piston handle is squeezed. The clips are advanced in the magazine by a resiliently biased pusher element.

The Leroy-Raney clip is a plastic spring clip with jaws which are normally biased toward one another. The jaws have rearward portions with protrusions which are adapted to be engaged by a scissors like applicator to pry the jaws apart. Through the applicator, the clips are applied in one-at-a-time fashion. After the application of each clip, a new clip must be singly loaded into the applicator.

A clip similar to the Leroy-Raney type may be seen from U.S. Pat. No. 4,217,902. FIGS. 1-3 of that patent show a clip with protrusions somewhat similar to those of the Leroy-Raney clip employed in the dispenser of the present invention. That patent also shows various scissor-type applicators for installing such clips in one-at-a-time fashion.

Other surgical clips employing jaws which are normally biased toward one another may be seen from U.S. Pat. No. 3,802,437 and West German Pat. No. 2730691. These clips are also designed to be applied in one-at-a-time fashion.

U.S. Pat. Nos. 4,508,253 and 4,530,453 are also considered of interest in that they relate to surgical clips arranged in magazine-like cartridges, and mechanical dispensers for these clips. The clips and dispensers are materially different from those forming the subject of the present application, however, in that they rely on anvil-like structures for their operation. U.S. Pat. No. 4,427,008 and the International Application published under No. WO 84/01280 on Apr. 12, 1984 are also of interest in that they disclose surgical clips contained in magazines. In the case of the latter patent and application, the clips are normally in an open condition and are latched into a closed condition during dispensing.

SUMMARY OF THE INVENTION

The dispenser of the present invention employs an elongated magazine for holding a plurality of clips. At one end, a discharge mechanism communicates with the magazine to direct clips out of the magazine while forcing the jaws of the clips into an open condition. The discharge mechanism has an open end through which the clips are ejected with the jaws in an open condition. Upon being so ejected, biasing means incorporated into the clips moves the jaws together and into engagement with the incision edge being treated. Guide surfaces at the end of the discharge opening are adapted to position the opening relative to the edge of an incision to be hemostatically clipped. The magazine is provided with resilient means to convey the clips to the discharge mechanism.

In the method of the invention, an incision to be hemostatically closed is spanned with the open distal end of a guide tube or tunnel. A clip having normally engaged spring biased jaws is then directed through the tunnel to spread the jaws. Upon being fully spread, the clip is discharged from the tunnel to release the jaws for engagement with the flesh member being treated.

A principal object of the invention is to provide a hemostatic clip dispenser and a method for applying hemostatic clips wherein multiple clips are contained within a magazine and dispensed therefrom in one-at-a-time fashion, without the requirement that the clips be pushed through the dispensing mechanism in tandem fashion.

Another object of the invention is to provide such a dispenser and method wherein standard "Leroy-Raney" clips may be employed.

Still another object of the invention is to provide such a dispenser and method wherein the jaws of normally closed spring-biased clips are first automatically spread and then released for hemostatic treatment.

Still another object of the invention is to provide such a dispenser and method wherein the incision being treated may be engaged and held in place during the application of the clips.

A further object of the invention is to provide such a dispenser and method wherein clips are contained within a magazine which is isolated from the dispensing mechanism during application of the individual clips.

These and other objects will become more apparent when viewed in light of the accompanying drawings and the following detailed description.

BRIEF DESCRIPTION OF THE DRAWINGS

FIG. 1 is a cross-sectional side elevational view of the dispenser, with the plunger in the condition it assumes immediately prior to the dispensing operation;

FIG. 2 is a perspective view of a "Leroy-Raney" clip, with the jaws thereof in the normally closed condition;

FIG. 3 is a perspective view of a "Leroy-Raney" clip, with the jaws thereof shown forced to an open condition;

FIGS. 4 and 5 are cross-sectional views taken on the planes designated by lines 4—4 and 5—5 of FIG. 1; and FIG. 6 is a cross-sectional side elevational view of the dispenser, with parts thereof broken away, illustrating the dispenser in the process of applying a clip to an incision in the flesh of the scalp.

DESCRIPTION OF THE PREFERRED EMBODIMENT

Referring now to FIG. 1, the dispenser is designated therein in its entirety by the letter "D." It comprises a body having a tubular magazine "M" extending vertically over the length of its forward side and a spring chamber "C" integrally joined to the magazine and extending vertically to the rear thereof. A tapered tunnel member "T" is releasably secured to the forward side of the magazine "M" in alignment with an opening 10 formed in the magazine. The top of the magazine is closed by an end wall 12. A cylindrical bearing 14 is carried by a top wall portion 16 formed on the spring chamber "C." The bearing 14 is axially aligned with the tunnel member "T" and slidably carries a cylindrical plunger or bar 18. The forward end of the bar 18 is concave and conformed to complimentally engage the rearward side of a clip received within the magazine "M" (see FIG. 6). The rearward end of the bar 18 carries a pin 19 pivotally received within a slot 20 formed in the top of a plunger handle "H." The bottom end of the plunger handle is pivotally supported by a pin 22 carried by a bifurcated mount 24 secured to the backside of the spring chamber "C." A compression coil spring 26 is interposed between the handle "H" and the backside of the chamber "C" to normally bias the handle "H" to the retracted position, as shown in FIG. 1.

The cross-sectional configuration of the magazine "M" and chamber "C" is illustrated in FIG. 4. There it will be seen that the magazine "M" is of a generally reverse C-shaped configuration with a vertical slot 28 opening into the chamber "C." Vertically extending ledges 30 are formed in the magazine "M" to either side of the slot 28. Vertically extending turned-in edges 32 are formed on the outside of the magazine and, together with the ledges 30 and the side walls of the magazine, define a chamber "S" for slidable receiving spring clips "L", as will become more apparent subsequently.

A follower 34 is slidably received in the magazine between the ledges 30. The rearward side of the follower is provided with a connector 36 which extends slidably through the slot 28 and is secured to a resilient silicone band 38. The band 38 extends over a sheave 40 rotabably secured in the top of the chamber "C" to secure connection with a fixed anchor 42 at the bottom of the chamber. The band serves as a spring and normally biases the follower 34 upwardly within the magazine "M." With the clips received within the magazine "M," as shown in FIGS. 1 and 6, this upward movement of the follower serves to force the clips "L" upwardly within the magazine.

An apertured latex diaphragm 44 is secured between the tunnel member "T" and the magazine "M" in alignment with the opening 10. This diaphragm serves to keep the topmost or leading clip in position within the magazine "M" until such time as the plunger 18 is depressed to force the clip out of the magazine and through the tunnel member "T."

The clips "L" are of the "Leroy-Raney" type and may best be seen from FIGS. 2 and 3. Each clip "L" is of a monolithic construction and fabricated of a plastic material such as nylon or polyvinyl chloride; and comprises opposed upper and lower jaw 46 and 48, respectively, connected together by a rearward section 50 which serves to bias the jaws together. The surfaces of the jaws intersect at the front of the clip to define clamping edges 52 and 54. Cylindrical protrusions 56 and 58 are formed on the outer surfaces of the jaws and provide gripping means whereby the jaws may be spread to the open condition, as shown in FIG. 3.

The releasable connection between the tunnel member "T" and the magazine "M" is provided by a hinge 60 and releasable fastener 62 (see FIG. 5). By releasing the fastener 62, the member "T" may be swung to one side, thus exposing the opening 10 so that clips may be loaded therethrough. The clips are loaded into the magazine through the opening 10 and forced down against the follower 34, as shown in FIGS. 1 and 6. The follower then functions to continuously exert an upward lifting force on the clips through means of the resilient band 38.

Once the clips are loaded into the magazine, the tunnel member "T" is swung to the closed position and fastened into place, as shown in FIGS. 5 and 6. With the dispenser so conditioned, the clips may be dispensed therefrom by simply depressing the handle "H" to force the plunger 18 through the bearing 14 and against the topmost or leading clip. Movement of the plunger 18 against the clip functions to force the clip through the diaphragm 44 and into the tunnel member "T." Converging internal cam surfaces 64 and 66 on the member "T" engage the protrusions 56 and 58 and force the clip to the open condition, as shown in FIG. 6. As a clip is discharged from the open distal end of the tunnel "T," designated 68, the clip is released and the jaws return to the closed condition (see FIG. 2).

The open distal end 68 is concave, as viewed in elevational (see FIGS. 5 and 6). This enables the end to span an incision in the flesh of the scalp, as shown in FIG. 6, and position the end relative to the edge of the incision. The scalp in FIG. 6 is designated by the numeral 70 and is shown as having flesh "F" with an incision formed therein having edges 72 and 74. The lowermost edge 74 is shown engaged between the jaws of the clip "L" being discharged from the tunnel member "T."

From the drawings, it will be appreciated that the magazine "M" is proportioned for slidable receipt of the clips "L." As received within the magazine, the protrusions 56 and 58 slide between the ledges 30 and the front surfaces of the clips slide along the edges 32. The rearward sides of the protrusions 56 and 58 slide along the surfaces of the magazine to either side of the slot 28. This overall arrangement assures that the clips will be disposed in the aligned condition shown in FIGS. 5 and 6 and will not cock and jamb within the magazine. It also assures that the follower 34 will move the clips upwardly to align the uppermost clip with the opening 10 for discharge by the plunger 18.

It will also be appreciated that the opening 10 and tunnel "T" are proportioned for the passage of the clips "L" therethrough in response to movement of the plunger 18. The opening in the diaphragm 44 is smaller than the clip "L" and spreads to accommodate such passage.

In operation, as can be seen from FIG. 6, the dispenser is first positioned so that the distal end of the tunnel member "T" spans the incision being treated. The plunger 18 is then depressed through means of the handle "H" to eject a clip from the magazine and through the tunnel member "T," thus spreading the jaws of the clip. Continued movement of the plunger to discharge the clip from the open distal end of the member "T" releases the clip so that the jaws may return to the closed condition, thus clamping the edge of the incision being treated. This procedure may be successively repeated along the length of the incision, whereby a plurality of clips may engage the edge of the flesh to either side of the incision.

CONCLUSION

From the foregoing description, it is believed apparent that the invention enables the attainment of the objects initially set forth herein. It should be understood, however, that the invention is not intended to be limited to the specifics of the illustrated embodiment, but rather is defined by the accompanying claims.

We claim:

1. A combination of jaw-type clips and an apparatus for dispensing the clips for use in achieving hemostasis along an incision edge, which comprises:
   (a) clips having upper and lower surfaces which intersect at one edge to form opposed jaws and diverge from said edge to a rearward section which joins said surfaces and biases said jaws together, said clips having external protrusions formed on said upper and lower surfaces adjacent said rearward section
   (b) an elongated magazine for holding at least two of said clips,
   (c) a guide tunnel disposed in intersecting communication with the magazine, said tunnel having an open distal end and tapered surfaces on the interior thereof converging from the magazine toward the distal end of the tunnel to engage the protrusions on a clip moved through the tunnel toward the open distal end thereof to force the jaws of the clip apart;
   (d) an elongated bar extensible through the magazine and tunnel for engagement with a clip held within the magazine to move the clip from the magazine and through the tunnel;
   (e) bar forwarding means to selectively advance the bar into engagement with a clip held within the magazine and force said clip through the tunnel for ejection from the distal end thereof in an open condition; and,
   (f) means for conveying said clips through said magazine to the intersection of the magazine and tunnel.

2. The combination of claim 1 wherein said bar forwarding means is selectively operable to permit said bar to be retracted for reloading of the magazine.

3. The combination of claim 1 further comprising diaphragm means between the magazine and tunnel to hold a clip within the magazine in alignment with the bar until the bar is advanced to push the clip into the tunnel.

4. The combination according to claim 1 wherein the guide tunnel is releasable from the magazine to open the magazine for the loading of clips thereto.

5. An improved method for hemostatically closing an incision in a flesh member, said method comprising:
   providing a guide tunnel having an open distal end and tapered internal cam surfaces which converge to said distal end;
   spanning the incision with the open distal end of the guide tunnel;
   directing a clip having a normally engaged spring biased jaws through the tunnel to engage protrusions on the jaws with the cam surfaces to force the jaws apart as the clips pass through the tunnel toward the open distal end thereof; and
   discharging said clip from the distal end of the tunnel to release the jaws for closure and engage the flesh member to either side of the incision between the jaws.

6. The improved method of claim 5 wherein said clip is contained in an elongated magazine communicating with said tunnel, and the clip is directed through the tunnel by forceably pushing the clip from the magazine and into and through the tunnel with a plunger.

7. The improved method of claim 5 wherein said incision is closed by successively repeating the improved method steps, whereby a plurality of said clips engages the flesh member on either side of the incision.

* * * * *